United States Patent
Wang

(10) Patent No.: US 11,246,797 B2
(45) Date of Patent: Feb. 15, 2022

(54) MASSAGE GLOVE AND VEHICLE-MOUNTED MASSAGE DEVICE

(71) Applicants: BOE TECHNOLOGY GROUP CO., LTD., Beijing (CN); BOE OPTICAL SCIENCE AND TECHNOLOGY CO., LTD., Jiangsu (CN)

(72) Inventor: Hongyun Wang, Beijing (CN)

(73) Assignees: BOE TECHNOLOGY GROUP CO., LTD., Beijing (CN); BOE OPTICAL SCIENCE AND TECHNOLOGY CO., LTD., Jiangsu (CN)

( * ) Notice: Subject to any disclaimer, the term of this patent is extended or adjusted under 35 U.S.C. 154(b) by 866 days.

(21) Appl. No.: 16/067,783

(22) PCT Filed: Dec. 18, 2017

(86) PCT No.: PCT/CN2017/116846
§ 371 (c)(1),
(2) Date: Jul. 2, 2018

(87) PCT Pub. No.: WO2018/218934
PCT Pub. Date: Dec. 6, 2018

(65) Prior Publication Data
US 2021/0169738 A1 Jun. 10, 2021

(30) Foreign Application Priority Data
May 27, 2017 (CN) .......................... 201710388726.0

(51) Int. Cl.
*A61H 39/04* (2006.01)
*A61H 23/02* (2006.01)

(52) U.S. Cl.
CPC ............. *A61H 39/04* (2013.01); *A61H 23/02* (2013.01); *A61H 2201/0157* (2013.01);
(Continued)

(58) Field of Classification Search
CPC .................... A61H 23/02; A61H 39/04; A61H 2201/0157; A61H 2201/165;
(Continued)

(56) References Cited

U.S. PATENT DOCUMENTS 9,579,060 B1 * 2/2017 Lisy ..................... A42B 3/0453
2008/0216207 A1 * 9/2008 Tsai ................... A61H 23/0263
2/160
(Continued)

FOREIGN PATENT DOCUMENTS

CN          101976495 A  *  2/2011
CN          101976495 A      2/2011
(Continued)

OTHER PUBLICATIONS

Second Office Action for Chinese Application No. 201710388726.0, dated Nov. 21, 2019, 8 Pages.
(Continued)

*Primary Examiner* — Tu A Vo
*Assistant Examiner* — Alexander Morales
(74) *Attorney, Agent, or Firm* — Brooks Kushman P.C.

(57) ABSTRACT

A massage glove and a vehicle-mounted massage device are provided. The massage glove includes a glove body, at least one acupuncture point massager and a controller. The acupuncture point massager is arranged on the glove body at a position corresponding to an acupuncture point on a hand. The acupuncture point massager is configured to massage the acupuncture point so as to relieve a physical fatigue of a user. The controller is configured to output a control signal to the acupuncture point massager, so as to enable the acupuncture point massager in accordance with the control signal.

13 Claims, 6 Drawing Sheets

(52) U.S. Cl.
CPC .... *A61H 2201/165* (2013.01); *A61H 2201/50* (2013.01); *A61H 2205/067* (2013.01); *A61H 2230/065* (2013.01); *A61H 2230/085* (2013.01); *A61H 2230/105* (2013.01)

(58) Field of Classification Search
CPC .......... A61H 2201/50; A61H 2205/067; A61H 2230/065; A61H 2230/085; A61H 2230/105
See application file for complete search history.

(56) References Cited

U.S. PATENT DOCUMENTS

| | | | | |
|---|---|---|---|---|
| 2010/0250179 | A1* | 9/2010 | Mariano | G01C 21/165 702/96 |
| 2010/0289346 | A1* | 11/2010 | Pepin | H02K 33/16 310/15 |
| 2013/0090581 | A1* | 4/2013 | Yamazaki | A41D 19/0024 601/81 |
| 2014/0350442 | A1* | 11/2014 | Park | A61H 39/002 601/48 |
| 2014/0375551 | A1* | 12/2014 | Oshita | G06F 3/016 345/156 |
| 2015/0032036 | A1 | 1/2015 | Brown et al. | |
| 2015/0213634 | A1* | 7/2015 | Karmarkar | A61B 5/163 345/589 |
| 2016/0113834 | A1* | 4/2016 | Bring | A61H 7/007 601/134 |
| 2016/0151238 | A1* | 6/2016 | Crunick | A61H 23/006 601/2 |
| 2016/0317382 | A1* | 11/2016 | Ode | A61H 9/0078 |
| 2017/0079537 | A1* | 3/2017 | McEwen | A61B 5/6828 |
| 2017/0258995 | A1* | 9/2017 | Hyde | H02K 33/16 310/15 |

FOREIGN PATENT DOCUMENTS

| | | |
|---|---|---|
| CN | 103049981 A | 4/2013 |
| CN | 103111020 A | 5/2013 |
| CN | 203226817 U | 10/2013 |
| CN | 103625288 A | 3/2014 |
| CN | 203713617 U | 7/2014 |
| CN | 104442991 A | 3/2015 |
| CN | 105105372 A | 12/2015 |
| CN | 105251120 A | 1/2016 |
| CN | 1058947332 A | 8/2016 |
| CN | 106056850 A | 10/2016 |
| CN | 106067256 A | 11/2016 |
| CN | 106157537 A | 11/2016 |
| CN | 106389097 A | 2/2017 |
| WO | WO-2017045290 A1 * | 3/2017 .............. G06F 3/039 |

OTHER PUBLICATIONS

International Search Report and Written Opinion for Application No. PCT/CN2017/116846, dated Mar. 14, 2018, 10 Pages.

* cited by examiner

MASSAGE GLOVE AND VEHICLE-MOUNTED MASSAGE DEVICE

CROSS-REFERENCE TO RELATED APPLICATIONS

This application is the U.S. national phase of PCT Application No. PCT/CN2017/116846 filed on Dec. 18, 2017, which claims priority to Chinese Patent Application No. 201710388726.0 filed on May 27, 2017, which are incorporated herein by reference in their entireties.

TECHNICAL FIELD

The present disclosure relates to a smart wearable device, in particular to a massage glove and a vehicle-mounted massage device.

BACKGROUND

Currently, traffic accidents due to fatigue driving happen occasionally. Especially when a driver is driving on highway, due to a dull environment, less interference, constant speed, few noises and vibration frequency, the driver may easily fall asleep. At this time, it is difficult for the driver to make judgment and decision normally, and any slight error may cause a serious traffic accident, Hence, how to prevent and relieve driving fatigue is very important to the driving security and has become the issue of wide concerns.

SUMMARY

An object of the present disclosure is to provide a massage glove and a vehicle-mounted massage device, so as to relieve the driving fatigue.

In one aspect, the present disclosure provides in some embodiments a massage glove, including a glove body, at least one acupuncture point massager and a controller. The acupuncture point massager is arranged on the glove body at a position corresponding to an acupuncture point on a hand. The controller is configured to output a control signal to the acupuncture point massager, to enable the acupuncture point massager in accordance with the control signal.

In a possible embodiment of the present disclosure, the acupuncture point massager is located at a position on the glove body corresponding to at least one of a thenar acupuncture point at the hand or a Shaochong acupuncture point on a little finger.

In a possible embodiment of the present disclosure, the massage glove further includes a timer arranged on the glove body, and configured to record a duration of a same action made by the hand of a user wearing the massage glove, and when the duration reaches a first time period, output a first triggering signal to the controller. The controller is further configured to output the control signal for enabling the acupuncture point massager in accordance with the first triggering signal.

In a possible embodiment of the present disclosure, the timer is further configured to record a duration of a driving action made by the hand of the user wearing the massage glove.

In a possible embodiment of the present disclosure, the massage glove further includes a speed detector arranged on the glove body, and configured to acquire a movement speed of the glove body, and when the movement speed is greater than or equal to a predetermined speed threshold, continuously output a second triggering signal. The timer is further configured to be enabled upon the receipt of the second triggering signal, disenabled when the second triggering signal is not received for a time period greater than a second time period, and acquire the duration of the driving action made by the hand of the user wearing the massage glove.

In a possible embodiment of the present disclosure, the massage glove further includes a manually-operated signal trigger arranged on the glove body, connected to the timer, and configured to output a signal to the timer, to start the timer in accordance with the signal from the signal trigger.

In a possible embodiment of the present disclosure, the controller is electrically connected to at least one fatigue monitor, and configured to receive a third triggering signal from the fatigue monitor, and output the control signal for enabling the acupuncture point massager in accordance with the third triggering signal.

In a possible embodiment of the present disclosure, the massage glove further includes a control switch connected between the controller and the acupuncture point massager.

In a possible embodiment of the present disclosure, the acupuncture point massager includes a power source electrically connected to the controller and a vibrator connected to the power source. The control signal from the controller is a square wave signal, and the power source is configured to output a current corresponding to the square wave signal and periodically varying in the form of a square ware to the vibrator, to enable the vibrator to generate vibration corresponding to a fluctuation period and an amplitude of the square wave signal.

In a possible embodiment of the present disclosure, the vibrator includes an electromagnet electrically connected to the power source, a vibrating body including a metal portion and located within a magnetic field generated by the electromagnet, and an elastic support member connected to the vibrating body. When the magnetic field is generated, the vibrating body is attracted by the electromagnet to move in a direction toward the electromagnet, the elastic support is compressed. When the magnetic field disappears, the vibrating body is not attracted by the electromagnet and moves in a direction away from the electromagnet under the effect of an elastic force of the elastic support member.

In a possible embodiment of the present disclosure, the elastic support member includes an elastic sheet or spring.

In another aspect, the present disclosure provides in some embodiments a vehicle-mounted massage device, including the above-mentioned massage glove and at least one wearable member on which at least one fatigue monitor is arranged. The fatigue monitor is configured to monitor a physiological feature parameter of a user wearing the wearable member, and when the physiological feature parameter indicates that the user is in a fatigue state, transmit a triggering signal to the controller of the massage glove. The controller is configured to output a control signal to the acupuncture point massager in accordance with the triggering signal.

In a possible embodiment of the present disclosure, the wearable member includes a hat, and the fatigue monitor is arranged on the hat and includes at least one of a brain wave detection member or an eye movement state detection member.

In a possible embodiment of the present disclosure, the wearable member includes a member capable of being worn on a body of the user, and the fatigue monitor is arranged on the member and includes at least one of a heart rate detection member or an electromyography (EMG) detection member.

In a possible embodiment of the present disclosure, the fatigue monitor includes an analysis circuit, a signal generation circuit and a signal transmission circuit. The analysis circuit is configured to determine a fatigue level of the user in accordance with the physiological feature parameter. The signal generation circuit is configured to generate a first square wave signal in accordance with the fatigue level. The signal transmission circuit is configured to transmit the first square wave signal, as the trigger signal, to the controller. The controller is further configured to generate the control signal in the form of a second square wave signal in accordance with the first square wave signal, and the second square ware signal has a fluctuation period and an amplitude each in direct proportion to the fatigue level.

In a possible embodiment of the present disclosure, the fatigue monitor is in wireless communication with the controller.

In yet another aspect, the present disclosure provides in some embodiments a massage glove, including a glove body, at least one acupuncture point massager, a processor, a memory and a computer program stored in the memory and capable of being executed by the processor. The computer program is executed by the processor, so as to output a control signal to the acupuncture point massager.

In still yet another aspect, the present disclosure provides in some embodiments a vehicle-mounted massage device, including at least one wearable member, a massage glove including a glove body and at least one acupuncture point massager, a processor, and at last one fatigue monitor arranged on the wearable member. The fatigue monitor is configured to monitor a physiological feature parameter of a user wearing the wearable member, and when the physiological feature parameter indicates that user is in a fatigue, transmit a triggering signal to the processor. The processor is configured to output a control signal to the acupuncture point massager in accordance with the triggering signal.

DETAILED DESCRIPTION

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

The present disclosure provides in some embodiments a massage glove, which includes a glove body, at least one acupuncture point massager and a controller.

The acupuncture point massager is arranged on the glove body at a position corresponding to a predetermined acupuncture point on a hand. The acupuncture point massager is configured to perform a massage operation on the predetermined acupuncture point, so as to relieve a physical fatigue of a user.

The controller is configured to output a control signal to the acupuncture point massager, so as to start the acupuncture point massager. In a possible embodiment of the present disclosure, the control signal may be used to enable, disenable or adjust the acupuncture point massager. Correspondingly, the acupuncture point massager may start, stop or adjust the massage operation in accordance with the control signal.

According to the massage glove in the embodiments of the present disclosure, based on a principle of relieving the physical fatigue through Chinese traditional massage, the massage operation may be performed on the predetermined acupuncture point on the hand through the acupuncture point massager, so as to relieve the physical fatigue of the user. The massage glove may be worn by a driver during a driving operation, so as to relieve the physical fatigue of the driver.

Figure 1:
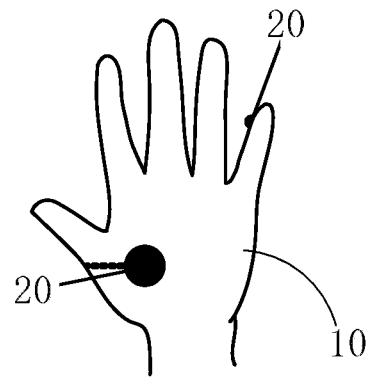
FIG. 1 is a schematic view showing a massage glove viewed from a side corresponding to a palm according to one embodiment of the present disclosure.
Figure 2:
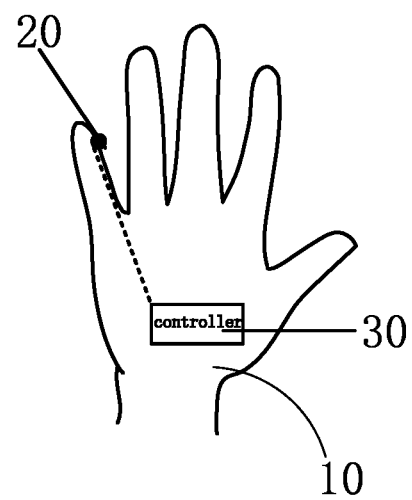
FIG. 2 is another schematic view showing the massage glove viewed from a side corresponding to a back of a hand according to one embodiment of the present disclosure.

As shown in FIGS. 1 and 2, in a possible embodiment of the present disclosure, the massage glove includes a glove body 10, an acupuncture point massager 20 and a controller 30. The acupuncture point massager 20 is arranged on the glove body 10 at a position corresponding to a predetermined acupuncture point on a hand.

In a possible embodiment of the present disclosure, the acupuncture point massager 20 is arranged at a position a position corresponding to a thenar acupuncture point on a palm and/or a Shaochong acupuncture point on a little finger. Based on a principle of the traditional Chinese medicine, the acupuncture points on the hand may be massaged so as to relieve the physical fatigue and prevent the driver from falling asleep. To be specific, the Shaochong acupuncture point on the hand may be massaged so as to relieve headache caused by the physical fatigue and refresh the driver's brain. The thenar acupuncture point may be massaged so as to enhance functions of the driver's spleen and stomach, thereby to prevent the driver from being a sleepy state. In a possible embodiment of the present disclosure, the acupuncture point massagers 20 may be arranged at the positions corresponding to the thenar acupuncture point and the Shaochong acupuncture point respectively, so as to further relieve the physical fatigue of the user.

As shown in FIGS. 1 and 2, the acupuncture point massager 20 corresponding to the thenar acupuncture point on the palm may be arranged at an inner surface of the glove body 10 at a side corresponding to the palm, so as to massage the thenar acupuncture point on the palm. The acupuncture point massager 20 corresponding to the Shaochong acupuncture point on the little finger may be arranged at the inner surface of the glove body 10 corresponding to the little finger, so as to massage the Shaochong acupuncture point on the little finger. In addition, the controller 30 may be arranged at the inner surface of the glove body 10 at a side corresponding to the back of the hand, and connected to each acupuncture point massager 20 on the glove body 10 via a circuit. Of course, the controller 30 may also be arranged at any other position on the glove body 10, e.g., at the inner surface of the glove body 10 at a side corresponding to the palm.

Figure 3:
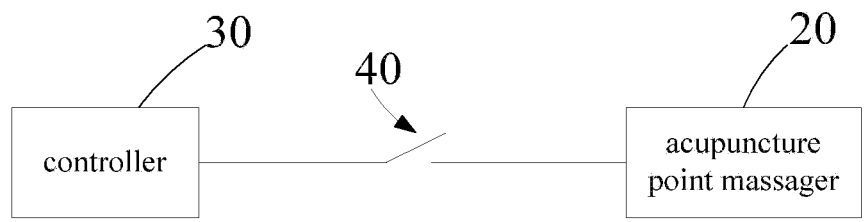
FIG. 3 is a schematic view showing a glove body of the massage glove according to a first embodiment of the present disclosure.

FIG. 3 is a schematic view showing the glove body of the massage glove according to a first embodiment of the present disclosure. In FIG. 3, apart from the acupuncture point massager 20 and the controller 30, the massage glove may further include a control switch 40 connected between the controller 30 and the acupuncture point massager 20.

To be specific, the control switch 40 may be arranged on the glove body 10. Through the control switch 40, it is able for the user to manually enable or disenable the acupuncture point massager 20.

Figure 4:
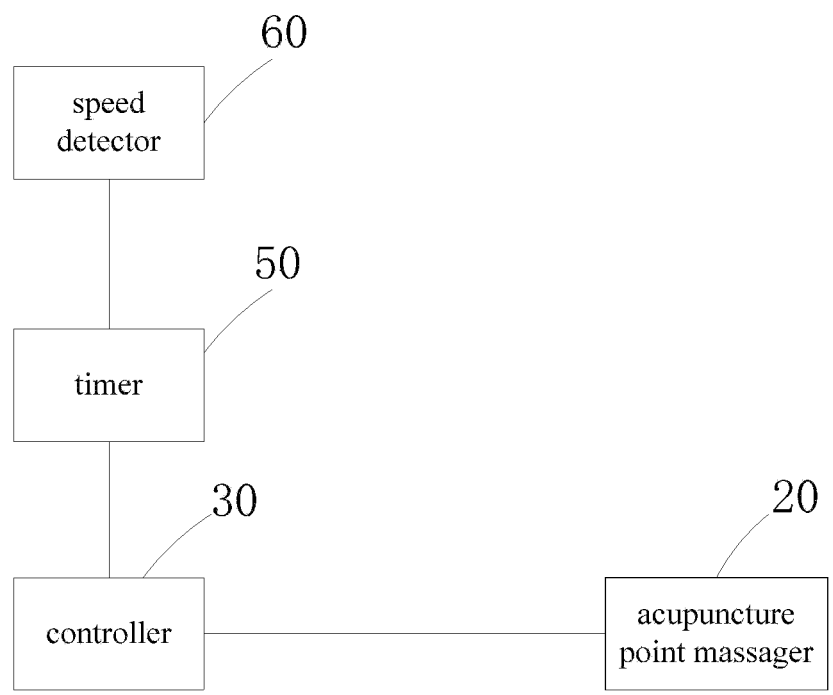
FIG. 4 is another schematic view showing the glove body of the massage glove according to a second embodiment of the present disclosure.

FIG. 4 is another schematic view showing the glove body of the massage glove according to a second embodiment of the present disclosure. In FIG. 4, apart from the acupuncture point massager 20 and the controller 30, the massage glove may further include a timer 50.

The timer 50 may be arranged on the glove body and configured to record a duration of a same action made by the hand of a user wearing the massage glove, i.e., a driving duration, and when the duration reaches a first time period, output a first triggering signal to the controller 30. The controller 30 is further configured to output the control signal in accordance with the first triggering signal, so as to enable the acupuncture point massager 20.

In a possible embodiment of the present disclosure, the massage glove may be worn by the driver during the driving operation, and the timer 50 may be configured to record a duration of a driving action made by the hand of the user wearing the massage glove.

To be specific, when the massage glove is worn by the driver during the driving operation, the first time period may be a time period within which the driver drives a vehicle continuously and becomes fatigue. Through the timer 50, it is able for the massage glove to record the driving duration of the driver, so as to monitor a fatigue state of the driver. When the driver is in or is about to be in the fatigue state, the acupuncture point massager 20 may be enabled in time, so as to effectively relieve the driving fatigue of the driver, thereby to prevent the occurrence of a traffic accident due to the driving fatigue.

In a possible embodiment of the present disclosure, as shown in FIG. 4, the massage glove may further include a speed detector 60 arranged on the glove body, and configured to acquire a movement speed of the glove body, and when the movement speed is greater than or equal to a speed threshold, continuously output a second triggering signal.

Upon the receipt of the second triggering signal, the timer 50 may be started, and when the second triggering signal is not received for a time period greater than a second time period, the timer 50 may be stopped. In this way, it is able to acquire the duration of the driving action made by the hand of the user wearing the massage glove, i.e., the driving duration of the vehicle.

To be specific, the speed threshold may be a normal running speed of the vehicle, e.g., greater than 10 km/h. Through the speed detector 60, when the movement speed of the massage glove is greater than or equal to 10 km/h, it is able to determine that the massage glove is worn by the driver who is just driving the vehicle. At this time, the speed detector 60 may continuously output the second triggering signal to the timer 50, so as to start the timer 50 and enable the timer 50 to record the driving duration.

In addition, when the second triggering signal is not received for a time period greater than the second time period, i.e., no second triggering signal is received within the second time period, it may be determined that the driver is currently not driving the vehicle. At this time, the timer 50 may be stopped. In a possible embodiment of the present disclosure, the second time period shall be greater than a shorter time period within which a running speed of the vehicle is smaller than the speed threshold due to a traffic jam, so as to prevent the timer from being stopped unexpectedly during the traffic jam.

In a possible embodiment of the present disclosure, the speed detector 60 may be in wireless communication with a speed sensor of the vehicle, and configured to acquire speed information about the vehicle detected by the speed sensor of the vehicle, so as to determine the movement speed of the glove body. When the movement speed of the glove body is greater than the speed threshold, the speed detector 60 may continuously output the second triggering signal to the timer 50, so as to enable the timer 50 to be started in accordance with the second triggering signal and thereby to record the driving duration.

Figure 5:
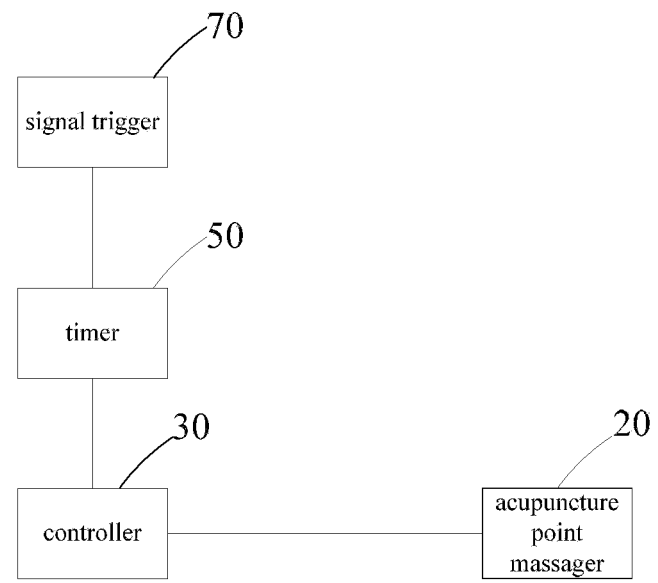
FIG. 5 is yet another schematic view showing the glove body of the massage glove according to a third embodiment of the present disclosure.

FIG. 5 is yet another schematic view showing the glove body of the massage glove according to a third embodiment of the present disclosure. In FIG. 5, apart from the acupuncture point massager 20 and the controller 30, the massage glove may further include the timer 50.

The timer 50 may be arranged on the glove body and configured to record a driving duration within which the driver wearing the massage glove drives the vehicle, and when the driving duration reaches the first time period, output a first triggering signal to the controller 30. The controller 30 is further configured to output the control signal in accordance with the first triggering signal, so as to enable the acupuncture point massager 20.

To be specific, the first time period may be a time period within which the driver drives a vehicle continuously and becomes fatigue. Through the timer 50, it is able for the massage glove to record the driving duration of the driver, so as to monitor a fatigue state of the driver. When the driver is in or is about to be in the fatigue state, the acupuncture point massager 20 may be enabled in time, so as to effectively relieve the driving fatigue of the driver, thereby to prevent the occurrence of a traffic accident due to the driving fatigue.

In a possible embodiment of the present disclosure, as shown in FIG. 5, the massage glove may further include a signal trigger 70 arranged on the glove body, connected to the timer 50, and configured to output a signal to the timer 50, so as to start the timer 50 in accordance with the signal from the signal trigger 70.

In the embodiments of the present disclosure, through the signal trigger 70, it is able for the driver wearing the massage glove to manually start the timer 50 at the beginning of the driving operation, thereby to monitor the fatigue driving state. A relationship between the signal trigger 70 and the timer 50 may be similar to an operation of setting an alarm on a mobile phone.

Figure 6:
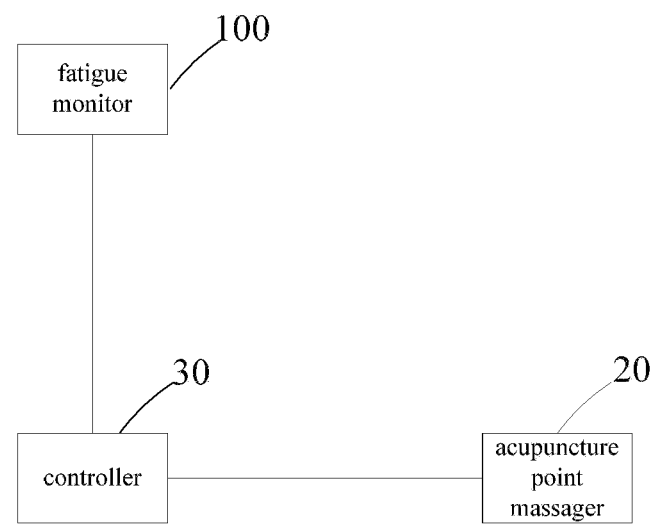
FIG. 6 is still yet another schematic view showing the glove body of the massage glove according to a fourth embodiment of the present disclosure.

FIG. 6 is still yet another schematic view showing the glove body of the massage glove according to a fourth embodiment of the present disclosure. In FIG. 6, on the basis of the acupuncture point massager 20 and the controller 30, the controller 30 is electrically connected to at least one fatigue monitor 100, and further configured to receive a third triggering signal from the fatigue monitor 100 and output a control signal to enable the acupuncture point massager 20 in accordance with the third triggering signal.

To be specific, the fatigue monitor 100 may be arranged on the wearable member worn by the user, and configured to monitor a physiological feature parameter of the user, and determine whether or not the user is in a fatigue state in accordance with the physiological feature parameter. When the user is in the fatigue state, the fatigue monitor 100 may transmit the third triggering signal to the controller 30 of the massage glove. The controller 30 may be further configured to output the control signal to the acupuncture point massager 20 in accordance with the triggering signal, so as to enable the acupuncture point massager 20.

In a possible embodiment of the present disclosure, the fatigue monitor 100 may include at least one of a brainwave detection member, an eye movement state detection member, a heart rate detection member and an EMG detection member.

In addition, the fatigue monitor 100 may be in wireless communication with the controller 30. A structure and an operating principle of the fatigue monitor 100 will be described hereinafter on the basis of a vehicle-mounted massage device.

Figure 7:
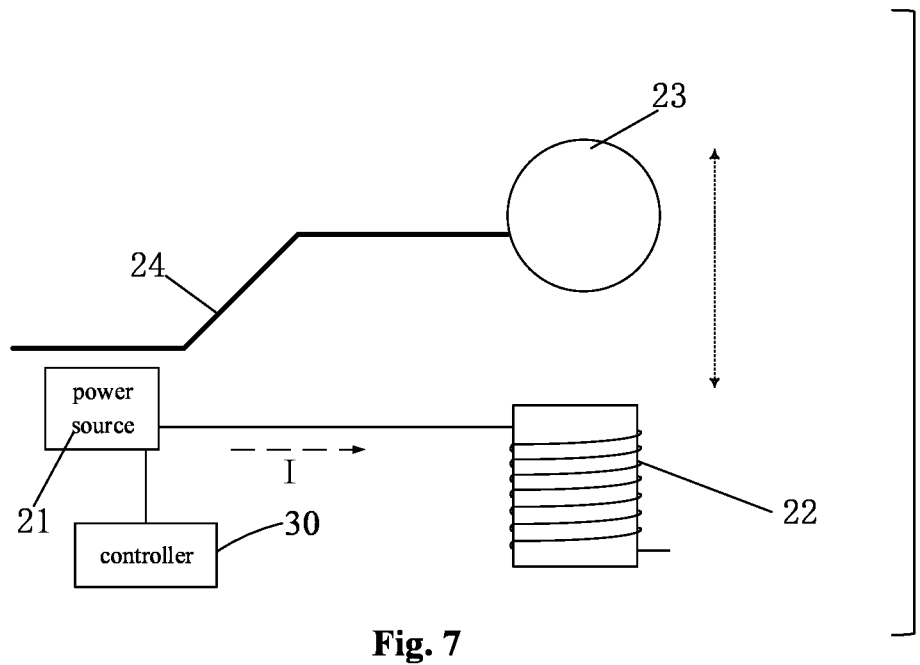
FIG. 7 is a schematic view showing an acupuncture point massager of the massage glove according to one embodiment of the present disclosure.

As shown in FIG. 7, the acupuncture point massager 20 may include a power source 21 connected to the controller 30 and a vibrator connected to the power source 21.

Figure 8:
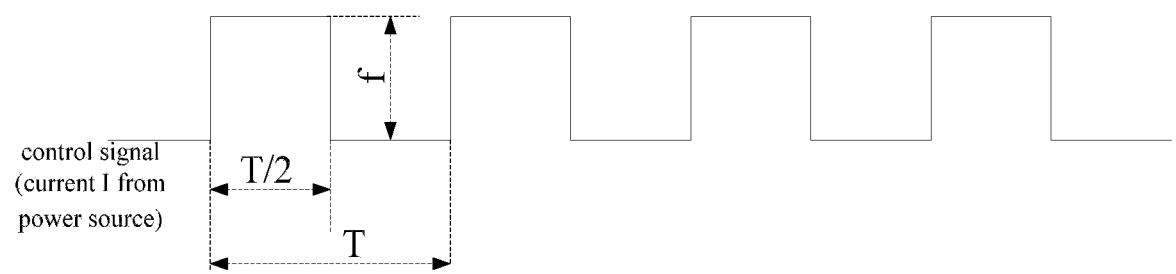
FIG. 8 is a waveform of a control signal from a controller of the massage glove according to one embodiment of the present disclosure.

In a possible embodiment of the present disclosure, the control signal from the controller 30 may be a square wave signal. As shown in FIG. 8, the square wave signal has a certain fluctuation period T and an amplitude f. The power source 21 may output a current in accordance with the square wave signal from the controller 30, i.e., the current generated by the power source 21 may also vary periodically in the form of the square wave signal. Within each fluctuation period T, when the control signal having the amplitude f is outputted within a first T/2 output period, the current from the power source 21 may be I, and when the control signal having the amplitude 0 is outputted within a second T/2 output period, the current from the power source 21 may be 0. In addition, a size of the current I from the power source 21 may be in direct proportion to the amplitude f of the control signal.

When the current is supplied to the vibrator, vibration may be generated by the vibrator, and a vibration period and a vibration amplitude may be in direct proportion to the fluctuation period T and the amplitude f of the control signal respectively.

To be specific, as shown in FIG. 7, the vibrator of the acupuncture point massager 20 includes an electromagnet 22, a vibrating body 23 including a metal portion, and an elastic support 24.

The electromagnet 22 is electrically connected to the power source 21. When the current is supplied by the power source 21 to the electromagnet 22, a magnetic field may be generated by the electromagnet 22.

The vibrating body 23 is located within the magnetic field generated by the electromagnet 22. When the magnetic field is generated, the vibrating body 23 may move in a direction toward the electromagnet 22, and when the magnetic field disappears, the vibrating body 23 may not be attracted by the electromagnet 22.

The elastic support 24 is connected to the vibrating body 23. When the magnetic field is generated, the vibrating body 23 may move in the direction toward the electromagnet 22, so as to compress the elastic support 24. When the magnetic field disappears, the vibrating body 23 may not be attracted by the electromagnet 22, and instead, it may move in a direction away from the electromagnet 22 under the effect of an elastic force generated by the elastic support 24.

Based on the acupuncture point massager 20 with the above-mentioned structure, the current periodically varying in the form of the square wave signal may be supplied by the power source 21 to the electromagnet 22. As shown in FIG. 8, within the first T/2 period of each fluctuation period T, the current I may be supplied by the power source 21 to the electromagnet 22, so as to generate the magnetic field by the electromagnet 22. At this time, the vibrating body 23 is located within the magnetic field and attracted by the electromagnet 22, so as to move in the direction toward the electromagnet 22, thereby to compress the elastic support 24. Within the second T/2 period, no current may be supplied by the power source 21 to the electromagnet 22. At this time, the magnetic field generated by the electromagnet 22 disappears, and the vibrating body 23 may move in the direction away from the electromagnet 22 under the effect of the elastic force generated by the elastic support 24.

In this way, the vibration may be generated by the vibrating body 23 through the movement in the direction toward and in the direction away from the electromagnet 22 in a reciprocating manner, so as to massage the predetermined acupuncture points on the hand. To be specific, when the current is supplied to the electromagnet 22 to generate the magnetic field, the vibrating body 23 may be attracted by the electromagnet 22. The larger the current supplied by the power source 21 is, the larger an intensity of the magnetic field generated by the electromagnet 22 is, the larger an attractive force applied to the vibrating body 23 is, and the larger a compression level of the elastic support 24 is. When no current is supplied to the electromagnet 22, the vibrating body 23 may move away from the electromagnet 22 under the effect of the elastic force generated by the elastic support 24, so as to massage the predetermined acupuncture points on the hand once. Based on the above-mentioned principle, a massage strength and a massage frequency of the predetermined acupuncture point are related to the fluctuation period T and the amplitude f of the control signal from the controller 30. Hence, it is able to adjust the acupuncture point massager 20 through adjusting the fluctuation period T and the amplitude f of the control signal from the controller 30.

Figure 11:
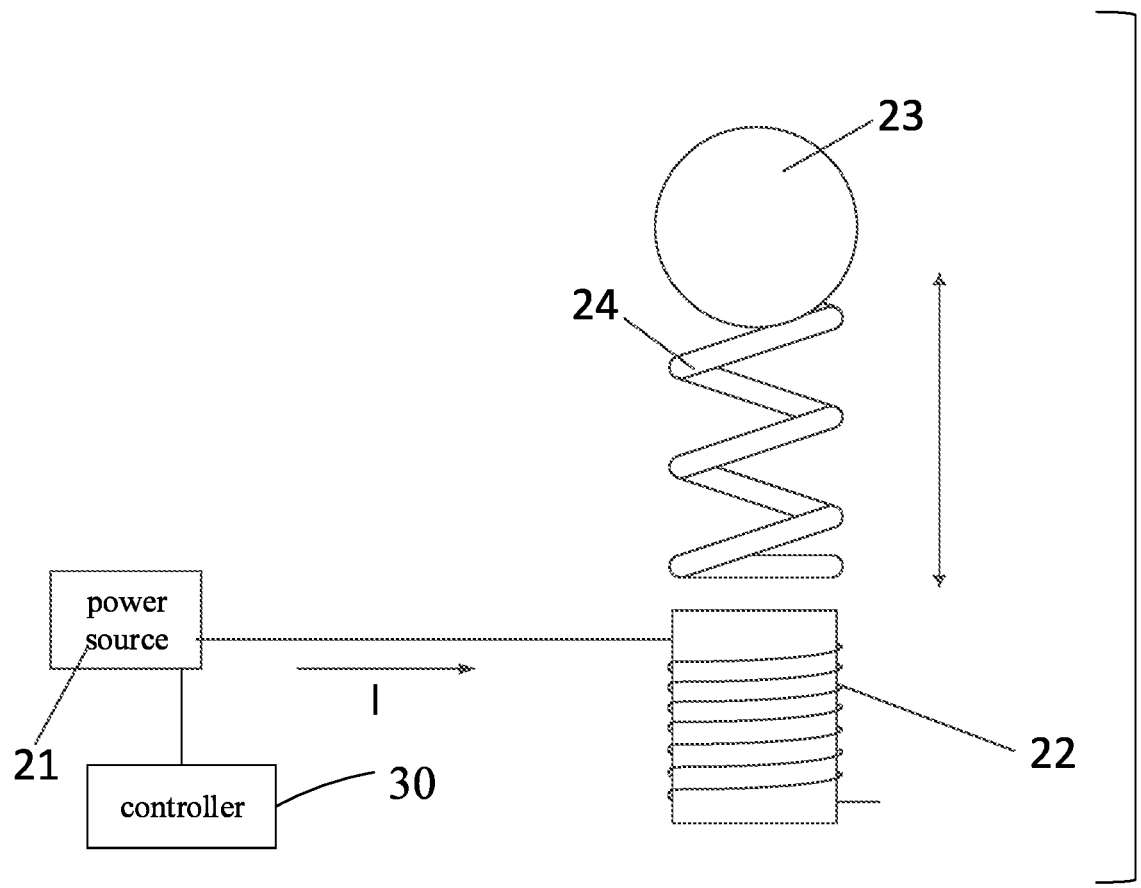
FIG. 11 is a schematic view showing the acupuncture point massager of the massage glove according to one embodiment of the present disclosure.

To be specific, the elastic support 24 may include elastic sheet (as shown in FIG. 7) or a spring (as shown in FIG. 11). Of course, the structure of the elastic support 24 may not be limited thereto, as long as it may elastically support the vibrating body 23.

According to the massage glove in the embodiments of the present disclosure, through the acupuncture point massager at the position corresponding to the predetermined acupuncture point, it is able to massage the predetermined acupuncture point, thereby to relieve the physical fatigue of the user.

The present disclosure further provides in some embodiments a vehicle-mounted massage device, including the above-mentioned massage glove and at least one wearable member on which at least one fatigue monitor is arranged. The fatigue monitor is configured to monitor a physiological feature parameter of a user wearing the wearable member, and when the physiological feature parameter indicates that the user is in a fatigue state, transmit a triggering signal to the controller of the massage glove. The controller is configured to output a control signal to the acupuncture point massager in accordance with the triggering signal.

The structure of the massage glove included in the vehicle-mounted massage device may refer to that mentioned above, and thus will not be particularly defined herein.

In addition, the wearable member of the vehicle-mounted massage device may include a hat, and the fatigue monitor may include a brain wave detection member and/or an eye movement state detection member arranged on the hat.

Figure 9:
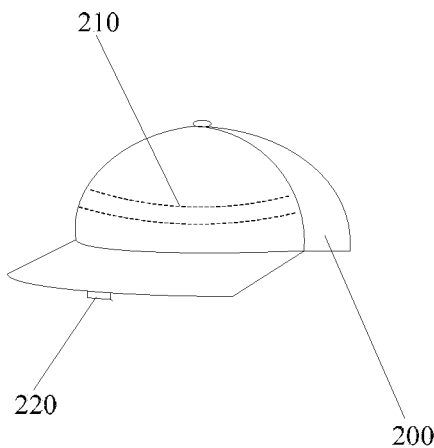
FIG. 9 is a schematic view showing a wearable member of a vehicle-mounted massage device according to one embodiment of the present disclosure.

To be specific, as shown in FIG. 9, the brain wave detection member 210 may be arranged at an inner surface of a hat body 200. When the hat is worn by the user, the brain wave detection member 210 may be in contact with a surface of the user's brain, so as to collect a brain wave signal, and determine whether or not the user is in a fatigue state in accordance with the collected brain wave signal.

In a possible embodiment of the present disclosure, the brain wave detection member may include at least one brain wave sensor configured to collect the brain wave signal of the user. In addition, the brain wave detection member may be further configured to analyze the brain wave signal collected by the brain wave sensor, so as to determine whether or not the user is in the fatigue state. For example, the brain wave detection member is further configured to compare the collected brain wave signal with a pre-stored fatigue-state brain wave signal, so as to determine whether or not the user is currently in the fatigue state. In a possible embodiment of the present disclosure, the brain wave detection member is further configured to determine a fatigue level of the user in accordance with the collected brain wave signal.

In addition, as shown in FIG. 9, the eye movement state detection member 220 may include a miniature camera arranged at a brim of the hat body 200, and configured to acquire an image of an eye of the user in real time, analyze an eye movement state in accordance with the image, and determine whether or not the user is in the fatigue state in accordance with the eye movement state. In a possible embodiment of the present disclosure, the eye movement state detection member 220 is further configured to determine the fatigue level of the user.

To be specific, the eye movement state detection member 220 may be configured to acquire a plurality of images of the eye of the user through the miniature camera, determine a blinking frequency and a real-time opening degree of the eye, compare the blinking frequency and the real-time opening degree of the eye with a predetermined blinking frequency and a predetermined opening degree of the eye in the fatigue state, and when the blinking frequency is greater than the predetermined blinking frequency and/or the real-time opening degree of the eye is smaller than the predetermined opening degree for a time period greater than a first time period, determine that the user is in the fatigue state.

In a possible embodiment of the present disclosure, through comparison results acquired by comparing the blinking frequency and the real-time opening degree of the eye with the predetermined blinking frequency and the predetermined opening degree of the eye in the fatigue state respectively, the eye movement state detection member may be further configured to determine the fatigue level of the user, e.g., to determine that the user is in a mild fatigue state, a moderate fatigue state or a heavy fatigue state.

In a possible embodiment of the present disclosure, when the wearable member includes both the brain wave detection member and the eye movement state detection member, they may be arranged independent of each other or connected to each other.

When the brain wave detection member and the eye movement state detection member are arranged independent of each other, they may be electrically connected to the controller of the massage glove. When the user is in the fatigue state in accordance with the monitored physiological feature parameter, the brain wave detection member and the eye movement state detection member may each transmit a triggering signal to the controller. The controller may then output the control signal to the acupuncture point massager upon the receipt of the triggering signal from any of them.

When the brain wave detection member and the eye movement state detection member are connected to each other, the wearable member may further include an analyzer configured to acquire detection data from the brain wave detection member and detection data from the eye movement state detection member, and analyze the acquired detection data so as to determine whether or not the user is in the fatigue state. When the user is in the fatigue state, the analyzer may transmit a triggering signal to the controller. The controller may then output the control signal to the acupuncture point massager in accordance with the received triggering signal.

In a possible embodiment of the present disclosure, the wearable member may further include a member capable of being worn on a body of the user, and the fatigue monitor may include a heart rate detection member and/or an EMG detection member.

To be specific, the member capable of being worn on the body of the user may be a jacket. The heart rate detection member may be arranged on an inner surface of the jacket at a position corresponding to the user's heart, and configured to collect a heart rate signal of the user and analyze the heart rate signal so as to determine whether or not the user is in the fatigue state. For example, the heart rate detection member may generate a heart rate waveform in accordance with the collected heart rate signal, and compare the resultant heart rate waveform with a pre-stored heart rate waveform in a normal state, so as to determine whether or not the user is currently in the fatigue state. In a possible embodiment of the present disclosure, the heart rate detection member may be further configured to determine the fatigue level of the user.

The EMG detection member may arranged at the inner surface of the jacket at a position corresponding to the user's arm, and configured to detect an EMG signal and analyze the collected EMG signal so as to determine whether or not the user is in the fatigue state. In a possible embodiment of the present disclosure, the EMG detection member may be further configured to determine the fatigue level of the user.

When the wearable member includes both the heart rate detection member and the EMG detection member, they may be arranged independent of each other or connected to each other.

When the heart rate detection member and the EMG detection member are arranged independent of each other and the user is in the fatigue state, they may each transmit a triggering signal to the controller. The controller may then output the control signal to the acupuncture point massager upon the receipt of the triggering signal from any of them.

When the heart rate detection member and the EMG detection member are connected to each other, the wearable member may further include an analyzer configured to acquire detection data from the heart rate detection member and detection data from the EMG detection member and analyze the acquired detection data, so as to determine whether or not the user is in the fatigue state. When the user is in the fatigue state, the analyzer may transmit a triggering signal to the controller. The controller may then output the control signal to the acupuncture point massager upon the receipt of the triggering signal.

In a possible embodiment of the present disclosure, the fatigue monitor may be in wireless communication with the controller of the massage glove. Upon the receipt of the triggering signal from the fatigue monitor or the triggering signal from the analyzer acquired in accordance with the detection data from the fatigue monitor, the controller may output the control signal to the acupuncture point massager, so as to enable the acupuncture point massager to generate the vibration at a predetermined vibration frequency or a predetermined vibration amplitude, thereby to massage the predetermined acupuncture point and relieve the physical fatigue of the user.

Figure 10:
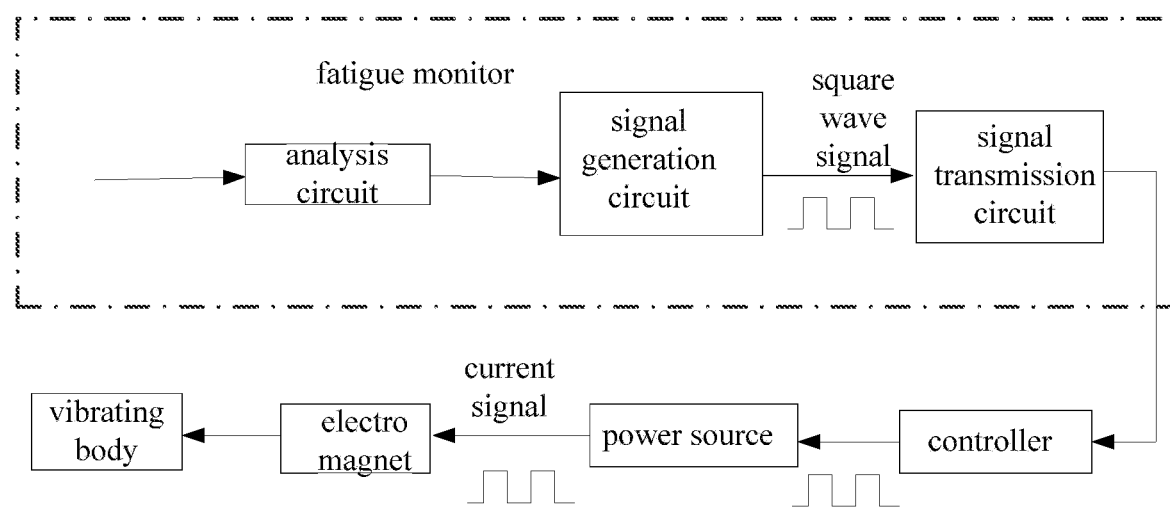
FIG. 10 is a schematic view showing signal transmission in the vehicle-mounted massage device according to one embodiment of the present disclosure.

In a possible embodiment of the present disclosure, as shown in FIG. 10, the fatigue monitor includes an analysis circuit, a signal generation circuit and a signal transmission circuit. The analysis circuit is configured to determine the fatigue level of the user in accordance with the physiological feature parameter, e.g., to determine whether or not the user is in the mild, moderate or heavy fatigue state. The signal generation circuit is configured to generate a first square wave signal in accordance with the fatigue level. To be specific, as shown in FIG. 8, the fluctuation period and amplitude of the first square wave signal are in direct proportion to the fatigue level acquired by the analysis circuit, i.e., the heavier the fatigue state is, the shorter the fluctuation period and the larger the amplitude are. The signal transmission circuit is configured to transmit the first square wave signal, as the trigger signal, to the controller. The controller is further configured to generate the control signal in the form of a second square wave signal in accordance with the first square wave signal from the signal transmission circuit, and the second square wave signal has a fluctuation period and an amplitude each in direct proportion to the fatigue level, i.e., the fluctuation period and the amplitude of the second square wave signal are in direct proportion to the fluctuation period and amplitude of the first square wave signal respectively.

Based on the above structure of the massage glove in conjunction with FIGS. 7 and 8, the controller of the massage glove is connected to the power source of the acupuncture point massager. When the control signal in the form of the square wave signal is outputted by the controller to the power source of the acupuncture point massager, the power source may output the current periodically varying in the form of a third square wave signal to the electromagnet. Similarly, a fluctuation period and an amplitude of the third square wave signal are in direct proportion to the fatigue level acquired by the fatigue monitor. At this time, the vibrating body may generate the vibration at a corresponding vibration frequency or amplitude, so as to massage the predetermined acupuncture point.

According to the vehicle-mounted massage device in the embodiments of the present disclosure, the wearable member including the fatigue monitor may analyze the fatigue state of the user in accordance with the physiological feature parameter of the user, determine the fatigue level of the user, and control the acupuncture point massager of the massage glove to massage the predetermined acupuncture point at the massage strength and the massage frequency in direct proportion to the fatigue level. As a result, it is able to relieve the physical fatigue of the user and perform the massage operation effectively. The vehicle-mounted massage device with the above-mentioned structure may be worn by the driver during the driving, so as to relieve the physical fatigue of the driver.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A massage glove, comprising a glove body, a timer, a speed detector, at least one acupuncture point massager and a controller, wherein the at least one acupuncture point massager is arranged on the glove body at a position corresponding to at least one acupuncture point on a hand, and the controller is configured to output a control signal to the at least one acupuncture point massager, to control the acupuncture point massager, the timer is arranged on the glove body and configured to record a duration of a driving action made by the hand of a user wearing the massage glove, and when the duration reaches a first time period, output a first triggering signal to the controller, wherein the controller is further configured to output the control signal for enabling the acupuncture point massager in accordance with the first triggering signal, the speed detector is arranged on the glove body, and configured to acquire a movement speed of the glove body, and when the movement speed is greater than or equal to a predetermined speed threshold, continuously output a second triggering signal, wherein the timer is further configured to be enabled upon the receipt of the second triggering signal, disenabled when the second triggering signal is not received for a time period greater than a second time period, and acquire the duration of the driving action made by the hand of the user wearing the massage glove.

2. The massage glove according to claim 1, wherein the at least one acupuncture point massager is located at the position corresponding to an acupuncture point on the hand correspond to at least one of a thenar acupuncture point at the hand or a Shaochong acupuncture point on a little finger.

3. The massage glove according to claim 1, further comprising a manually-operated signal trigger arranged on the glove body, connected to the timer, and configured to output a signal to the timer, to start the timer in accordance with the signal from the signal trigger.

4. The massage glove according to claim 1, wherein the controller is electrically connected to at least one fatigue monitor, and configured to receive a third triggering signal from the fatigue monitor, and output the control signal for enabling the acupuncture point massager in accordance with the third triggering signal.

5. The massage glove according to claim 1, further comprising a control switch connected between the controller and the acupuncture point massager.

6. The massage glove according to claim 1, wherein the acupuncture point massager comprises a power source electrically connected to the controller and a vibrator connected to the power source, the control signal from the controller is a square wave signal, and the power source is configured to output a current corresponding to the square wave signal and periodically varying in a form of a square wave to the vibrator, to enable the vibrator to generate vibration corresponding to a fluctuation period and an amplitude of the square wave signal.

7. The massage glove according to claim 6, wherein the vibrator comprises an electromagnet electrically connected to the power source, a vibrating body comprising a metal portion and located within a magnetic field generated by the electromagnet, and an elastic support member connected to the vibrating body,
wherein when the magnetic field is generated, the vibrating body is attracted by the electromagnet to move in a direction toward the electromagnet, the elastic support member is compressed, and when the magnetic field disappears, the vibrating body is not attracted by the electromagnet and moves in a direction away from the electromagnet under the effect of an elastic force of the elastic support member.

8. The massage glove according to claim 7, wherein the elastic support member comprises an elastic sheet or spring.

9. A vehicle-mounted massage device, comprising the massage glove according to claim 1 and at least one wearable member on which at least one fatigue monitor is arranged, wherein;
the fatigue monitor is configured to monitor a physiological feature parameter of a user wearing the at least one wearable member, and when the physiological feature parameter indicates that the user is in a fatigue state, transmit a third triggering signal to the controller of the massage glove; and
the controller is configured to output the control signal to the acupuncture point massager in accordance with the third triggering signal.

10. The vehicle-mounted massage device according to claim 9, wherein the at least one wearable member comprises a hat, and the fatigue monitor is arranged on the hat and comprises at least one of a brain wave detection member or an eye movement state detection member.

11. The vehicle-mounted massage device according to claim 9, wherein the at least one wearable member comprises a member capable of being worn on a body of the user, and the fatigue monitor is arranged on the member and comprises at least one of a heart rate detection member or an electromyography (EMG) detection member.

12. The vehicle-mounted massage device according to claim 9, wherein the fatigue monitor comprises an analysis circuit, a signal generation circuit and a signal transmission circuit;
the analysis circuit is configured to determine a fatigue level of the user in accordance with the physiological feature parameter;
the signal generation circuit is configured to generate a first square wave signal in accordance with the fatigue level;
the signal transmission circuit is configured to transmit the first square wave signal, as the third triggering signal, to the controller; and
the controller is further configured to generate the control signal in the form of a second square wave signal in accordance with the first square wave signal, and the second square wave signal has a fluctuation period and an amplitude each in direct proportion to the fatigue level.

13. The vehicle-mounted massage device according to claim 9, wherein the fatigue monitor is in wireless communication with the controller.

* * * * *